United States Patent [19]
Lu

[11] Patent Number: 5,476,482
[45] Date of Patent: Dec. 19, 1995

[54] PACEMAKER PROGRAMMER-BASED AUTOMATIC RETROGRADE CONDUCTION MEASUREMENT

[75] Inventor: Richard Lu, Highlands Ranch, Colo.

[73] Assignee: Telectronics Pacing Systems, Inc., Englewood, Colo.

[21] Appl. No.: 226,175

[22] Filed: Apr. 12, 1994

[51] Int. Cl.⁶ ..................................... A61N 1/36
[52] U.S. Cl. ................................. 607/9; 607/25
[58] Field of Search ..................... 607/9, 14, 25, 607/27; 128/697, 703, 705

[56] References Cited

U.S. PATENT DOCUMENTS

| | | | |
|---|---|---|---|
| 4,505,276 | 3/1985 | Markowitz et al. | 607/27 X |
| 4,539,991 | 9/1985 | Boute et al. | 607/9 |
| 5,074,308 | 12/1991 | Sholder et al. | 607/27 X |
| 5,167,224 | 12/1992 | Limuosin et al. | 607/14 |

OTHER PUBLICATIONS

Littleford et al., "Paumoker-Mediated Tachycardias: A Rapid Bedside Technique for Induction and Observation", The American Journal of Cardiology pp. 287–291 vol. 52 Aug. 1983.

Seymour Furman, MD, et al. A Practice of Cardiac Pacing pp. 65–68, Futura Publishing Company, Inc. Mount Kisco, N.Y. 1986.

*Primary Examiner*—George Manuel
*Assistant Examiner*—Jeffrey R. Jastrzab
*Attorney, Agent, or Firm*—Gottlieb, Rackman & Reisman

[57] ABSTRACT

A method for automatically determining the existence of retrograde conduction in a pacemaker patient. At a selected ventricular pacing rate, A-senses are detected, and V-pace to A-sense intervals are measured. If the measured intervals are consistent, it is possible that there is retrograde conduction. To confirm that the A-senses were not due to noise, atrial premature beats, etc., subsequent ventricular pacing pulses are generated in a manner that eliminates the possibility of atrial beats being due to retrograde conduction; a series of simultaneous atrial and ventricular pacing pulses are generated. If A-senses consistent with the previously measured intervals are not sensed, retrograde conduction is confirmed.

30 Claims, 2 Drawing Sheets

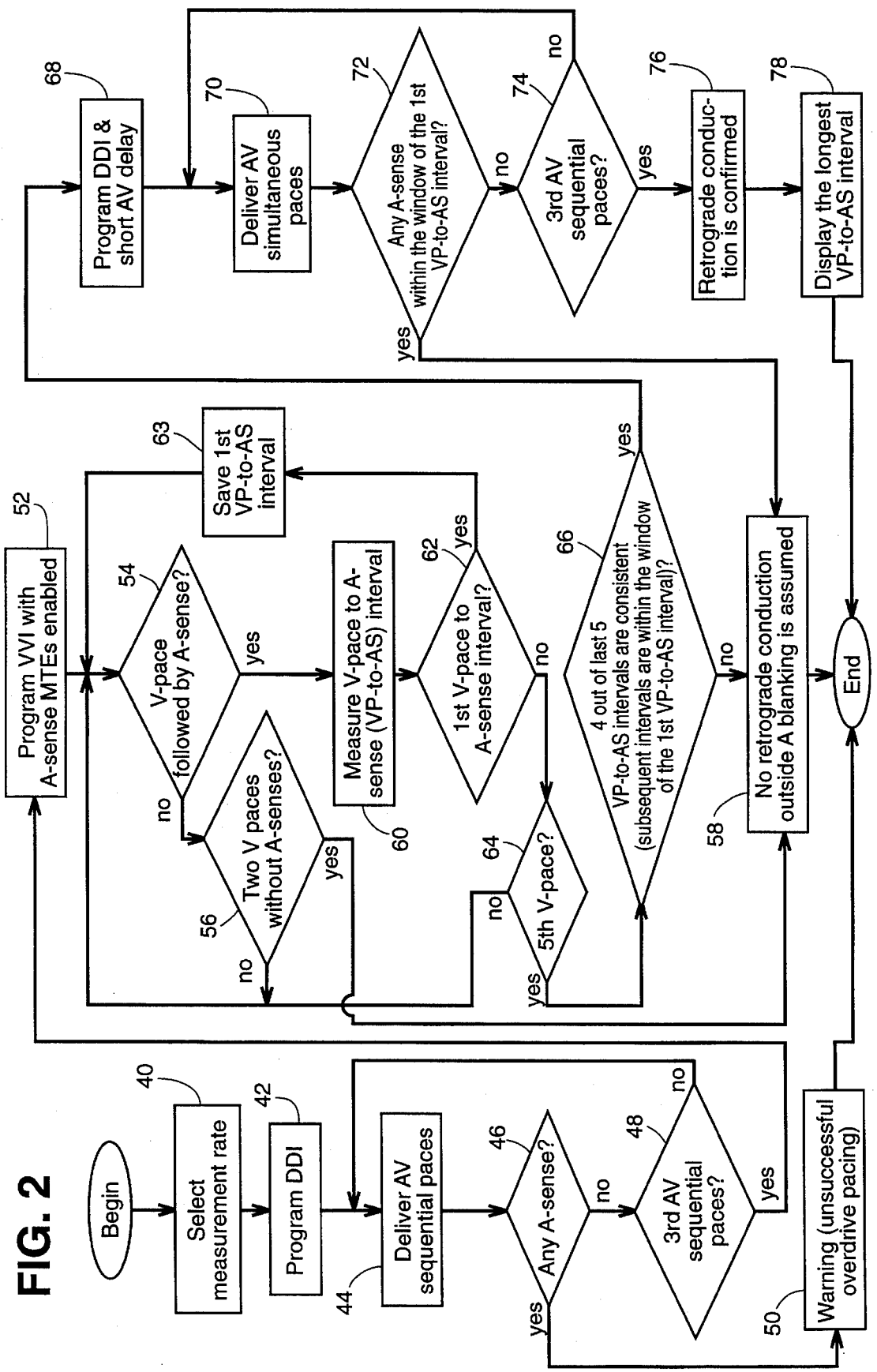

PACEMAKER PROGRAMMER-BASED AUTOMATIC RETROGRADE CONDUCTION MEASUREMENT

FIELD OF THE INVENTION

This invention relates to heart pacemakers, and more particularly to the automatic measurement of patient retrograde conduction using a physician-operated pacemaker programmer.

BACKGROUND OF THE INVENTION

Measurement of retrograde conduction during pacemaker implant has demonstrated that 45% of patients who require pacemaker implantation for any indication—ventricular or supraventricular tachycardia, sinus node dysfunction or AV block—have retrograde conduction at some paced rate if paced from the ventricle. Sixty-seven percent of patients paced for sinus node dysfunction have retrograde conduction, and 14% of those with fixed complete antegrade heart block have retrograde conduction. Even patients who have had AV block for many years may retain retrograde conduction. The mean retrograde conduction time from the ventricular stimulus to the atrial intrinsic deflection is 235±50 ms and the range is 110 ms to 450 ms. [See Furman and Holmes, *A Practice of Cardiac Pacing*, Futura Publishing Co., New York 1989, pp. 66–67.] During pacemaker implants and follow-ups, the measurement of retrograde conduction intervals could allow for the setting of the appropriate postventricular atrial refractory period (PVARP) to avoid retrograde conduction causing the onset of pacemaker mediated tachycardia (PMT).

The existence of retrograde conduction via the natural pathway, and the antegrade conduction via the implanted dual-chamber pacemaker, provide a reentry circuit that mimics the natural situation in which an accessory pathway allows a circus movement tachycardia. This reentry tachycardia, PMT, may occur when a P-wave displaced from its natural position before the QRS complex is tracked in the ventricle. The P-wave can be displaced by a ventricular premature contraction or ventricular stimulus with retrograde conduction. If the displaced P-wave falls within the atrial refractory period, it will not be tracked and no further event will occur. On the other hand, if the displaced P-wave falls outside the atrial refractory period, it will begin an AV interval and be tracked in the ventricle. If retrograde conduction exists, another P-wave will occur following the ventricular stimulus, and the reentry loop will be sustained.

If retrograde conduction exists, PMT can be prevented by programming the PVARP longer than the retrograde conduction interval. The retrograde conduction time begins with a ventricular event. The retrograde conduction time ends when a retrograde P-wave occurs (assuming that the retrograde conduction results in an atrial event). The PVARP interval similarly begins with the ventricular event. Thus, PMT can be prevented by making the PVARP interval longer than the retrograde conduction interval because the atrial event will not be tracked (although it can be sensed) if it occurs during the PVARP. On the other hand, higher tracking rates can be programmed if the PVARP is shortened. Therefore, to provide an optimal trade-off between these two factors, the retrograde conduction interval should be measured if it exists.

At the present time, retrograde conduction intervals are determined manually by reprogramming the pacemaker to some special parameter settings. For example, the pacemaker can be programmed to operate in the VDD mode, with a long PVARP to prevent the occurrence of PMT. During the test, there is certainly no desire to trigger PMT so a relatively long PVARP is programmed. The mode is set to VDD because ventricular pacing (V) is desired since each retrograde conduction interval to be measured begins with a ventricular event, but both chambers are sensed (the first D) because atrial sensing is required in order to determine if a retrograde P-wave is present and in order to measure the retrograde conduction time; there is no tracking of the sensed retrograde P-wave because the retrograde P-wave occurs during the PVARP and thus there is no triggering of an AV delay. Ventricular overdrive pacing (a fast pacing rate) is employed to facilitate retrograde conduction if it exists. (Early ventricular beats occur when the atria are not likely to be refractory so that retrograde conduction is possible. It is for a similar reason that retrograde conduction, which can give rise to PMT, usually occurs after a premature ventricular contraction.) Typically, retrograde conduction intervals can be measured manually by observing main timing events (MTEs) and/or a surface ECG and/or the telemetered intracardiac ECG on the programmer display. The manual determination of retrograde conduction intervals in current pacemaker systems is often quite time consuming. Not surprisingly, retrograde conduction intervals are rarely determined at most clinical centers. Patient safety is potentially compromised if the PVARP parameter is not programmed appropriately.

SUMMARY OF THE INVENTION

The invention is an apparatus and method for automatically confirming the presence of retrograde conduction and, if desired, also measuring the retrograde conduction time. In the preferred embodiment, the technique is programmer-based in that the measurement is controlled by the programmer which the physician ordinarily uses to program pacemaker parameters. The automatic measurement decreases the implant or follow-up time that is necessary to determine the retrograde conduction interval so that the PVARP parameter can be programmed appropriately to avoid PMT.

In the preferred embodiment of the invention, the pacemaker is first temporarily programmed to a dual-chamber overdrive pacing mode, e.g., DDI. An overdrive pacing rate is selected for the entire test, and a number of pacing cycles take place. The overdrive pacing in both chambers during the initial steps is designed to eliminate intrinsic beats. Typically, the first step lasts for three pacing cycles.

In the second step, the pacemaker is programmed to the VVI mode (this can be done automatically by the programmer, or internally by the pacemaker), with atrial sense MTEs enabled at the previously selected overdrive pacing rate. The retrograde conduction time is rate dependent. The faster the pacing rate, the longer the retrograde conduction time. The retrograde conduction time measurement is therefore preferably performed at various possible pacing rates. The longest retrograde conduction interval can be used to determine the ultimate PVARP setting. Enabling atrial sense MTEs allows a determination of when atrial beats occur. The VVI mode is the mode in which only ventricular sensing and pacing occurs. By enabling atrial sense MTEs, the effective mode is VDI (the D represents atrial as well as ventricular sensing).

During a number of pacing cycles, for example, 5 cycles, a check is made to see whether an atrial sense MTE follows a ventricular pace before the next ventricular pace or before 500 ms have elapsed, whichever is greater. (If the atrial sense occurs more than 500 ms after the ventricular pace, then it is unlikely to be due to retrograde conduction.) Of course, the programmer only looks for atrial beats outside the usual cross-channel blanking interval (typically, 150 ms in the Model 1254). The reason for this is that there is often a far-field R-wave signal. Consequently, the atrial channel may pick up a signal immediately following a ventricular beat. To sense atrial events accurately, the atrial sense channel is enabled only after a blanking interval. The V-Pace to A-Sense interval (VP-to-AS interval) is measured during each cycle. If 4 out of 5 VP-to-AS intervals are within ±20 ms of the first VP-to-AS interval, then retrograde conduction may be occurring. The basic test here is to look for consistency in VP-to-AS intervals.

It should be noted that even if an atrial event occurs during the PVARP, it will be sensed, although it will not trigger an AV delay. A-sensing is critical because without it there is no indication of retrograde conduction possibly taking place. It should also be appreciated that using a cross-channel blanking interval of 150 ms ensures that far-field R-wave signals do not pose a problem—far-field effects should be less than the blanking period; it is only retrograde conduction that can be longer, perhaps 200–450 ms. (The reason for the retrograde conduction time being longer is that retrograde conduction is through the AV node which slows down electrical conduction.)

The reason for the initial test to determine whether there are at least 4 out of 5 (in general, X out of Y) atrial senses following ventricular paces with consistent VP-to-AS intervals is that if this condition does not exist, it is unlikely that there is retrograde conduction outside the blanking period. If the test is passed, however, it simply means that there may be retrograde conduction. The atrial senses may still be due to noise or some other cause.

In the third step, the programmer reprograms the pacemaker to the DDI mode with an AV delay of 0 ms (or the shortest available AV delay, but preferably no longer than 20 ms), and at the previously selected overdrive pacing rate for three pacing cycles. The simultaneous, or near simultaneous, pacing of both chambers blocks retrograde conduction. The simultaneous pacing in both chambers is important. It is in this step that confirmation of retrograde conduction is accomplished. If there are no atrial senses following ventricular paces that result in VP-to-AS intervals within ±20 ms of the first VP-to-AS interval measured in the second step, then it is confirmed that the previous VP-to-AS intervals were due to retrograde conduction. In the absence of retrograde conduction, i.e., in the presence of noise, A-senses may still be detected. If atrial events are not sensed, however, it is due to the fact that the simultaneous pacing of both chambers prevents retrograde conduction, proving that when atrial events were previously sensed, in the absence of simultaneous pacing, the reason must have been retrograde conduction. Preferably, the check in this step is that there are no atrial senses at all that result in the previously first measured VP-to-AS interval, within ±20 ms. In general, the presence of retrograde conduction is confirmed only if during this step, the pattern of atrial beats is markedly different from the pattern of atrial beats sensed in the preceding step when it was concluded that retrograde conduction may be present.

The programmer can report to the physician the longest VP-to-AS interval measured during the second step as the retrograde conduction interval at the pacing rate under consideration. The absence of retrograde conduction is assumed if the tests in the second and third steps are not passed, i.e., the consistent atrial events of the second step are not seen or, if they are, atrial senses are detected in the third step. The test can be repeated at other pacing rates chosen by the physician.

At the end of the test, the pacemaker returns to the previously programmed values under control of the programmer or the pacemaker. At any time during the test, the test can be aborted by pressing an appropriate key on the programmer. If the test is manually aborted, simultaneous A and V paces should take place (i.e., the shortest possible AV delay) before the pacemaker returns to the previously programmed values. The reason for this is that if the test is aborted during the time that retrograde conduction is occurring and the operating mode is DDD, an atrial event will be sensed in the atrial channel due to the retrograde conduction and PMT may be induced. Causing both chambers to beat simultaneously blocks any possible retrograde conduction.

BRIEF DESCRIPTION OF THE DRAWINGS

Further features and advantages of this invention will become apparent upon consideration of the following detailed description in conjunction with the drawing, in which:

FIG. 2 is a flow chart of the algorithm used in the system of FIG. 1 to automatically confirm the presence of retrograde conduction and measure its duration.

DESCRIPTION OF THE INVENTION

Figure 1:
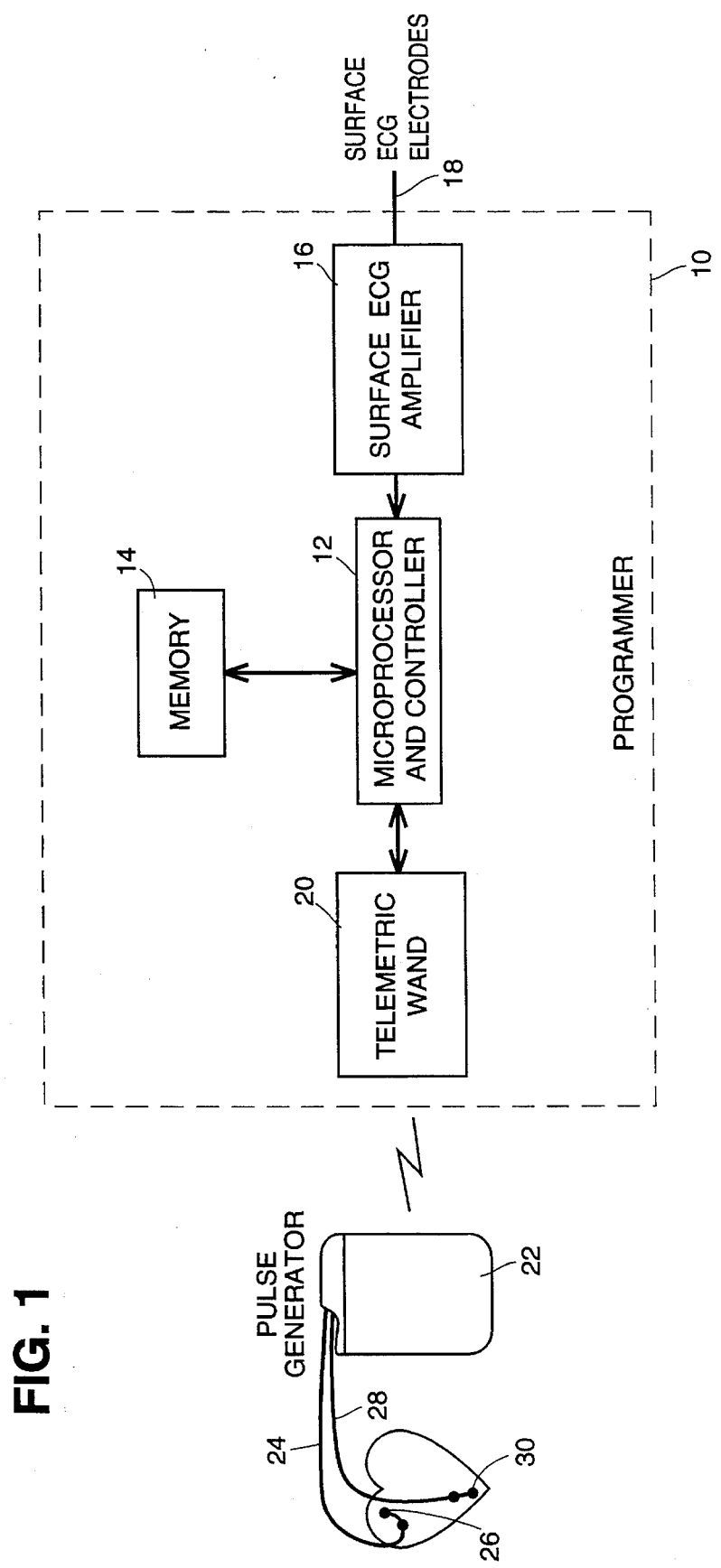
FIG. 1 is a block diagram of the hardware system of the invention including a programmer and an implanted pulse generator.

The hardware system shown in FIG. 1 comprises a programmer 10, which includes a microprocessor and controller 12, a memory 14, a surface electrocardiographic amplifier 16 having a patient cable 18 with surface ECG electrodes (not shown), and a telemetric wand 20. A pulse generator 22 (pacemaker) is implanted in the patient and is here shown as having an atrial lead 24 with an electrode 26 located adjacent to the muscle wall of the right atrium, and a ventricular lead 28 with an electrode 30 located adjacent to the muscle wall of the right ventricle. An exemplary programmer is the 9600 Network Programmer, manufactured by Telectronics Pacing Systems which is a combined programmer/ECG monitor and recorder and has several replaceable memory cassettes which contain the operating software and data storage memory required for different pacemakers. An exemplary pulse generator is the META DDDR Model 1254 dual chamber, rate responsive, multi-programmable, cardiac pulse generator with telemetry and a range of functions which includes fourteen pacing modes. An exemplary ventricular lead is a Telectronics Accufix Model 330-201, and an exemplary atrial lead is a Telectronics Accufix Model 330-801.

At the start of the test procedure, an overdrive measurement rate is selected in step 40 of FIG. 2. Overdrive pacing occurs so that there are no intrinsic beats. In step 42, the pacemaker is programmed to operate in the DDI mode. In step 44, a number of sequential AV pacing pulses are delivered for the purpose of giving rise to stable cycling without any intrinsic beats.

In step 46, a check is made to see whether an atrial event (A-sense) occurs following each pair of atrial and ventricular pulses. (As described above, the test for an A-sense is made only outside the atrial channel blanking interval, since the far-field R-wave signal may result in the pacemaker thinking that it has sensed an intrinsic atrial beat if the atrial channel is not blanked for about 150 ms following a ventricular pacing pulse.) If an atrial beat is detected, the physician is informed in step 50 by the programmer that the overdrive pacing has not eliminated intrinsic beats and the test procedure is aborted. The test may be reinitiated with a higher overdrive pacing rate. On the other hand, if following each pair of atrial and ventricular paces an A-sense is not detected in step 46, a check is made in step 48 whether three pairs of pacing pulses have yet been delivered. If they have not, a return is made to step 44 at which time another pair of pacing pulses is generated. When three pairs of atrial and ventricular pulses have been generated without any A-senses having been detected, i.e., the overdrive pacing is successful, and a stable beating action has been set in place, then the actual detection of the retrograde conduction time begins at step 52. The preliminary sequencing discussed thus far is designed primarily to ensure that overdrive pacing is operative, and that there is a stable beating of the patient's heart.

If the overdrive pacing is successful, then in step 52 the pacemaker is programmed to operate in the WI mode at the previously selected rate, with A-sense MTEs enabled. As discussed above, this in effect gives rise to operation in the VDI mode (atrial and ventricular sensing, but ventricular pacing only). The pacemaker telemeters out to the programmer, for display to the physician, every sensing of an atrial beat, as well as the generation of every ventricular pacing pulse. Although automatic processing of a surface ECG can be used to detect V-paces and A-senses, it is difficult to do the latter and it is advantageous to make use of the MTE capability already in place. Following each V-pace, it is determined in step 54 whether an A-sense occurs outside the cross-channel blanking interval. If there is no A-sense following a V-pace, but in step 56 it is determined that this is not the second cycle in which this has happened, then a return is made to step 54 where the same test is performed in the next cycle, for the next V-pace. On the other hand, if there have been two cycles in which V-paces have not been followed by A-senses, it is an indication that there is no retrograde conduction (i.e., no A-senses after atrial blanking), a determination made in step 58. The test procedure comes to an end because most likely there is no retrograde conduction, and therefore no measurement is required.

It is only if an A-sense follows a V-pace, as determined in step 54, that there may be retrograde conduction so that a measurement should be taken. In step 60, the interval between the V-pace and A-sense events is measured. The VP-to-AS interval measured in the first cycle is used as a standard against which subsequent VP-to-AS intervals are compared. If there is retrograde conduction, there should be consistency in the VP-to-AS intervals. In step 62, a check is made to see whether the interval just measured is the first. If it is, then in step 63 the current VP-to-AS interval is registered as the first interval, and it is thereafter used as the standard for subsequent measured intervals. The system then returns to step 54 to await the next cycle.

On the other hand, if the VP-to-AS interval just measured is not the first, then the test in step 66 is performed. It is here that a decision may be made that retrograde conduction is not occurring, and that previously detected A-senses were due to noise or some other cause. The decision is not made that retrograde conduction is occurring. If the possibility of retrograde conduction is not excluded, then it may be present, but it still must be confirmed.

But before step 66 is performed, it must be determined that five V-paces have taken place. This is accomplished in step 64. If five V-paces have not occurred, a return is made to step 54. Otherwise, the "consistency" test in step 66 is performed.

In step 66, each current VP-to-AS interval is compared with the first interval saved in step 63. Any current interval is consistent with the first interval if it is within ±20 ms of the first interval. If four out of the last five intervals are consistent, then retrograde conduction may be occurring, and the system advances to step 68. On the other hand, if four out of the last five measured intervals are not consistent, it is assumed that there is no retrograde conduction because VP-to-AS intervals are generally consistent when there is retrograde conduction. Consequently, in step 58 a determination is made that there is no retrograde conduction interval to measure and the sequence concludes.

Just because a number of P-waves have been sensed at consistent intervals after preceding ventricular paces is not a guarantee that retrograde conduction is really occurring. It may be that noise has been sensed and there is no retrograde conduction. As the preceding sequencing takes place, the longest VP-to-AS interval is registered and, if there is retrograde conduction, then this is the interval which is reported to the physician in step 78—the longest interval is desired because the PVARP should be programmed to exceed this interval. But before the longest interval is reported, a check is made that there really is retrograde conduction. What is done is similar to the initial sequencing—the pacemaker is programmed so that there is almost certainly no retrograde conduction; if A-senses are still detected within the window of the first VP-to-AS interval, then what is really being sensed is most likely noise, not the effects of retrograde conduction.

In step 68, the pacemaker is programmed to the DDI mode with a short AV delay, preferably a delay of 0 ms. With an AV delay of 0 ms (some pacemakers such as the Model 1254 of Telectronics Pacing Systems provide such a setting for diagnostic purposes), both chambers beat simultaneously. Even with a 20 ms AV delay, the beats are approximately simultaneous. The reason for using such a short AV delay is that if there is retrograde conduction, the desire is to reduce its effect by causing the atrial refractory period to begin as late in the overall cycle as possible, i.e., with the retrograde conduction. In this way, any conduction in the reverse direction will arrive at the atria when they are still refractory. Also, causing the atria and ventricles to beat together in step 70 results in collisions of the respective wavefronts and blocks retrograde conduction from occurring in the first place.

If during any of three cycles an A-sense is sensed within the window of the first VP-to-AS interval (see step 63), then a branch is made to step 58 where it is established that there is no retrograde conduction. On the other hand, if in any cycle an A-sense is not detected, then a check is made in step 74 to see whether three cycles have transpired since the initial branch from step 64. If three cycles have not taken place, a branch is made to step 70 where the next pair of atrial and ventricular pacing pulses are generated. When three cycles have transpired without any A-senses having been detected where they previously were detected, i.e., within the window of the first VP-to-AS interval, then it is an indication that the previously detected A-senses (processed in steps 54–64) were indeed due to retrograde conduction. Confirmation takes place in step 76, and the longest VP-to-AS interval is displayed in step 78.

The cycling on the right side of FIG. 2 is particularly important because of the uncertainty inherent in the VP-to-AS interval measurements. Unless there is a way to ensure that A-senses are not the result of noise, the measurements are unreliable, not to mention the determination that retrograde conduction is even present. It is in the final sequencing that a check is made that there is no noise. The simultaneous pacing of the atria and ventricles should result in the VA pathway being refractory so that atrial retrograde beats from ventricular stimuli cannot occur. If atrial senses still occur following simultaneous atrial and ventricular pacing, then the atrial sensed beats must be from other sources (e.g., noise, atrial premature beats, etc.) and there are no atrial beats resulting from retrograde conduction.

The flow chart of FIG. 2 depicts the sequencing for one selected measurement rate (see step 40). Preferably, retrograde conduction measurements may be made at different pacing rates. Succeeding tests at different pacing rates may be performed automatically, rather than to require the physician to program a different pacing rate and to re-initiate the test every time that a new test rate is desired. For example, it is possible to provide a button on the programmer which when operated by the physician automatically increases the rate by 10 pulses per minute, and then re-initiates the test.

It should be noted that in step 52 the pacemaker is programmed to operate in the VVI mode with A-sensing enabled. This in effect converts the VVI mode to a VDI mode. If a particular pacemaker cannot be programmed to the VDI mode, the VDD mode should be used. The difference between the two modes is that in the VDD mode, every A-sense results in the triggering of an AV delay so that V-paces track A-senses. Such tracking is not needed or desired when performing the test sequence. In fact, such tracking can give rise to PMT being induced during the test sequence, and to avoid this from happening the pacemaker should be programmed to have the longest possible PVARP at the selected pacing rate. This will ensure that while A-senses are used to terminate each VP-to-AS interval measurement, they do not trigger AV delays and V-paces.

The confirmation process of the subject invention can be used to advantage in confirming the presence of, and terminating, PMT. A pacemaker in which this is done is disclosed in my co-pending application entitled "APPARATUS AND METHOD FOR DETECTING, CONFIRMING AND TERMINATING PACEMAKER MEDIATED TACHYCARDIA", U.S. Ser. No. 227,306, filed on even date herewith and assigned to the assignee of this application. My aforesaid co-pending application is hereby incorporated by reference.

Although the invention has been described with reference to a particular embodiment, it is to be understood that this embodiment is merely illustrative of the application of the principles of the invention. For example, the entire test routine can be performed internally by the pacemaker. The advantage of using the programmer, however, is that it allows the physician to determine to his own satisfaction that he is setting an appropriate PVARP (although the pacemaker could also self-adjust its PVARP). Thus it is to be understood that numerous modifications may be made in the illustrative embodiment of the invention and other arrangements may be devised without departing from the spirit and scope of the invention.

What is claimed is:

1. A method of automatically confirming the presence of retrograde conduction in a pacemaker patient comprising the steps of:

(a) generating a series of first ventricular pacing pulses and sensing a succeeding atrial beat, (b) measuring intervals between each of said first ventricular pacing pulses and said succeeding sensed atrial beat, (c) determining whether said intervals are consistent, (d) if said intervals are consistent, then generating several second ventricular pacing pulses in a manner that reduces the effect of retrograde conduction, and (e) confirming that retrograde conduction is present only if, while step (d) is performed, atrial beats are not sensed after one of said intervals following said second ventricular pacing pulses.

2. A method in accordance with claim 1 wherein, upon confirmation that retrograde conduction is present, a longest interval measured in step (b) is registered as a retrograde conduction time.

3. A method in accordance with claim wherein step (d) further comprises the step of generating an atrial pulse approximately simultaneously with each second ventricular pacing pulse.

4. A method in accordance with claim 3 wherein in step (e) the presence of retrograde conduction is confirmed only if atrial beats are not sensed at the ends of all of the measured intervals following said several second ventricular pacing pulses.

5. A method in accordance with claim 4 further comprising performing the method by an external programmer controlling a pacemaker and determining pacemaker operation through telemetry from the pacemaker, and operating said pacemaker in steps (d) and (e) at an overdrive rate and with a very short AV delay.

6. A method in accordance with claim 5 further comprising performing steps (a)–(c) at a selected ventricular pacing rate, with the method being repeated for different ventricular pacing rates so that a largest retrograde conduction time for all of said ventricular pacing rates can be determined.

7. A method in accordance with claim 5 further comprising performing in step (c) a measurement of a first V-pace-to-A-sense (VP-to-AS) interval for one first ventricular pacing pulse, and determining whether X out of Y VP-to-AS intervals are within a window around said one VP-to-AS interval.

8. A method in accordance with claim 7 wherein said X out of Y is determined using Y=X+1.

9. A method in accordance with claim 5 further comprising, prior to performance of step (a), generating a number of overdrive ventricular pacing pulses to stabilize a beating action of a patient's heart.

10. A method in accordance with claim 9 further comprising not performing steps (a)–(e) if an atrial beat outside an atrial blanking period is detected following any overdrive ventricular pacing pulse.

11. A method in accordance with claim 1 further comprising generating in step (d) an atrial pacing pulse approximately simultaneously with each second ventricular pacing pulse.

12. A method in accordance with claim 11 further comprising confirming in step (e) the presence of retrograde conduction only if atrial beats are not sensed after said intervals following said several second ventricular pacing pulses.

13. A method in accordance with claim 12 further comprising performing the method by an external programmer controlling a pacemaker and determining pacemaker operation through telemetry from the pacemaker, and operating said pacemaker in steps (d) and (e) at an overdrive rate and with a very short AV delay.

14. A method in accordance with claim 13 further comprising performing steps (a)–(c) at a selected ventricular pacing rate, with the method being repeated for different ventricular pacing rates so that a largest retrograde conduction time for all of said ventricular pacing rates can be determined.

15. A method in accordance with claim 12 further comprising measuring in step (c) a first V-pace-to-A-sense (VP-to-AS) interval for one first ventricular pacing pulse, and determining whether X out of Y VP-to-AS intervals are within a window around said first VP-to-AS interval.

16. A method in accordance with claim 15 wherein in said determining step X, and Y are determined using Y= X+1.

17. A method in accordance with claim 1 further comprising the step of confirming in step (e) the presence of retrograde conduction only if atrial beats are not sensed after said intervals following said several second ventricular pacing pulses.

18. A method in accordance with claim 17 comprising performing the method by an external programmer controlling a pacemaker and determining pacemaker operation through telemetry from the pacemaker.

19. A method in accordance with claim 17 comprising performing steps (a)–(c) at a selected ventricular pacing rate, with the method being repeated for different ventricular pacing rates so that a largest retrograde conduction time for all of said ventricular pacing rates can be determined.

20. A method in accordance with claim 17 comprising measuring in step (c) a first V-pace-to-A-sense (VP-to-AS) interval for one ventricular pacing pulse, and determining whether X out of Y VP-to-AS intervals are within a window around said first VP-to-AS interval.

21. A method in accordance with claim 17, comprising generating prior to performance of step (a), a number of overdrive ventricular pacing pulses to stabilize a beating action of a patient's heart.

22. A method in accordance with claim 21 comprising not performing steps (a)–(e) if an atrial beat outside an atrial blanking period is detected following any overdrive ventricular pacing pulse.

23. A method in accordance with claim 1 comprising performing the method by an external programmer controlling a pacemaker and determining pacemaker operation through telemetry from the pacemaker, and operating said pacemaker in steps (d) and (e) at an overdrive rate and with a very short AV delay.

24. A method in accordance with claim 23 comprising performing the method at a selected ventricular pacing rate, with the method being repeated for different ventricular pacing rates so that a largest retrograde conduction time for all of said ventricular pacing rates can be determined.

25. A method in accordance with claim 23 comprising measuring in step (c) a first V-pace-to-A-sense (VP-to-AS) interval for one ventricular pacing pulse, and determining whether X out of Y VP-to-AS intervals are within a window around said first VP-to-AS interval.

26. A method in accordance with claim 1 comprising measuring in step (c) a first V-pace-to-A-sense (VP-to-AS) interval for a one ventricular pacing pulse, and whether X out of Y VP-to-AS intervals are within a window around said first VP-to-AS interval.

27. A method in accordance with claim 26, comprising generating prior to performance of step (a), a number of overdrive ventricular pacing pulses to stabilize a beating action of the patient's heart.

28. A method in accordance with claim 27 comprising not performing steps (a)–(e) if an atrial beat outside an atrial blanking period is detected following any overdrive ventricular pacing pulse.

29. A method in accordance with claim 1, comprising generating prior to performance of step (a), a number of overdrive ventricular pacing pulses to stabilize a beating action of a patient's heart.

30. A method in accordance with claim 29 comprising not performing steps (a)–(e) if an atrial beat outside an atrial blanking period is detected following any overdrive ventricular pacing pulse.

* * * * *